United States Patent
Korobkov et al.

(10) Patent No.: US 10,078,002 B2
(45) Date of Patent: Sep. 18, 2018

(54) METHOD FOR ESTIMATING THERMODYNAMIC EQUILIBRIUM OF A GAS-LIQUID MIXTURE DURING FILTRATION EXPERIMENTS

(71) Applicant: SCHLUMBERGER TECHNOLOGY CORPORATION, Sugar Land, TX (US)

(72) Inventors: Dmitry Alexandrovich Korobkov, Moscow (RU); Andrey Vladimirovich Kazak, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 338 days.

(21) Appl. No.: 14/406,662

(22) PCT Filed: Jun. 7, 2013

(86) PCT No.: PCT/RU2013/000475
§ 371 (c)(1),
(2) Date: Dec. 9, 2014

(87) PCT Pub. No.: WO2013/184041
PCT Pub. Date: Dec. 12, 2013

(65) Prior Publication Data
US 2015/0185064 A1    Jul. 2, 2015

(30) Foreign Application Priority Data
Jun. 9, 2012  (RU) .................................. 2012123865

(51) Int. Cl.
*G01F 23/296*    (2006.01)
*G01N 7/10*    (2006.01)
(Continued)

(52) U.S. Cl.
CPC ............ *G01F 23/296* (2013.01); *G01F 15/08* (2013.01); *G01N 7/10* (2013.01); *G01N 11/00* (2013.01)

(58) Field of Classification Search
CPC ........ G01N 7/10; G01N 11/00; G01F 23/296; G01F 15/08
(Continued)

(56) References Cited

U.S. PATENT DOCUMENTS

2011/0040501 A1*  2/2011  Martin .................... E21B 47/10
                                                                702/45

FOREIGN PATENT DOCUMENTS

RU    2171844 C2    8/2001
RU    2319111 C2    3/2010
(Continued)

OTHER PUBLICATIONS

International Search Report for corresponding PCT Application No. PCT/RU2013000475 dated Nov. 21, 2013.
(Continued)

*Primary Examiner* — Yoshihisa Ishizuka

(57) ABSTRACT

A gas phase and a liquid phase with a specified volumetric ratio of phases in a flow and with specified flow rates are injected into a multiphase separator. During the injection gas and liquid phase volumes in the separator are determined and accumulation rates of each phase in the separator are calculated. A thermodynamic equilibrium is estimated based on a discrepancy between the phase injection rates and the calculated phase accumulation rates.

4 Claims, 2 Drawing Sheets

(51) Int. Cl.
*G01F 15/08* (2006.01)
*G01N 11/00* (2006.01)

(58) Field of Classification Search
USPC .......................................................... 702/50
See application file for complete search history.

(56) References Cited

FOREIGN PATENT DOCUMENTS

| VG | GB 2417913 A | * | 3/2006 | ........... B01D 17/085 |
|----|--------------|---|--------|-------------------------|
| WO | 2011061210 A1 | | 5/2011 | |

OTHER PUBLICATIONS

Calisgan, et al, "Near Critical Gas Condensate Relative Permeability of Carbonates", The Open Petroleum Eng. Journal, (2008), pp. 30-41.
Chen, et al, "Determination of Relative Permeability and Recovery for North Sea Gas-Condensate Reservoirs", SPE Reservoir Eval. & Gen. 2 (4), (1999) pp. 393-402.
Jamiolahmady, et al, "Gas Condensate Relative Permeabilities in Propped Fracture Porous Media: Coupling Inertia", SPE 115726, (2008) 16 pages.
Al-Anazi, et al., "Laboratory Measurements of Condensate Blocking and Treatment for Both Low and High Permeability Rocks", Society of Petroleum Engineers, SPE-77546-MS, (2001) 9 pages.

* cited by examiner

METHOD FOR ESTIMATING THERMODYNAMIC EQUILIBRIUM OF A GAS-LIQUID MIXTURE DURING FILTRATION EXPERIMENTS

This application is a U.S. National Stage Application of International Application No. PCT/RU2013/000475, filed Jun. 7, 2013, which claims priority to Russian Application No. 2012123865, filed Jun. 9, 2012.

FIELD OF THE INVENTION

The invention relates to methods for experimental studying of gas-liquid mixture filtration and can be used, for example, in laboratories specialized in special core analysis, particularly in the measurement of phase permeabilities during multiphase filtration of mixable fluids (for example, a gas condensate mixture) through cores of rocks.

BACKGROUND ART

When performing a multiphase core flooding experiment, the quality of fluids' preparation is of great importance. Unlike single-phase core flood, to measure relative permeability of each fluid it's crucial to have all fluids in thermodynamic equilibrium, which is determined by pressure and temperature stabilization. The situation becomes critical when a fluid pair is gas and its condensate—gas and liquid phases of very similar physical properties. If the phases are not in the thermodynamic equilibrium, then decrease in volume of one phase takes place along with increase in volume of other phases. The latter circumstance makes it practically impossible to pump each of phases in a monitored manner at a fixed rate of volume flow.

Usually, a fluid pair gas-condensate is prepared in either a thermodynamic cell (a PVT-cell, a PVT bomb) or in a special container (a tank) at certain specified pressure and temperature. The thermodynamic equilibrium for fixed pressure and temperature is considered to be achieved after pressure stabilization of phases. For various reasons, it may be convenient to separate phases (liquid and gas) into different containers for experimental studies.

The need for transportation and storage of containers with separated phases often occurs, for example, for movement from a fluid thermodynamic study laboratory to a core flooding (filtration) laboratory. In this case, the thermodynamic disequilibrium is likely to occur due to variations of external conditions (temperature, pressure, mechanical effect). Even after a long time after the temperature stabilization in the containers, the phases after mixing thereof will most probably come out of the thermodynamic equilibrium state and will not achieve the initial state (which was after preparation of the equilibrium gas condensate mixture). As a result, the fluid pair injected into the core can be out of thermodynamic equilibrium.

In case of gas-condensate pair, this effect is expressed in occurrence of phase transitions: from a gas into a liquid and vice versa. As a consequence, a volumetric phase ratio specified in injection pumps may significantly differ from a volumetric phase ratio for a fluid before entering a core. In practice, it is suggested that fluids entering a core are already in the thermodynamic equilibrium which, as a rule, is not checked.

All existing experiments for filtration of a gas condensate mixture through cores can be divided into two groups: injecting a mixture in a single-phase (gaseous) state followed by separation into gas and liquid phases and by accumulation of the liquid phase (a gas condensate) in the core due to a pressure drop caused by filtration; and separate injection of both—gas and liquid—phases simultaneously with different volumetric fractions in a flow into a core. If a goal of the filtration experiment is to determine phase permeabilities, then, the most reasonable option is simultaneous injection of both—gas and liquid—phases that are in thermodynamic equilibrium.

Some researchers (cf., H. Calisgan and S. Akin, Near Critical Gas Condensate Relative Permeability of Carbonates, The Open Petroleum Engineering Journal, 1, 30-41 1874-8341/08, 2008, Bentham) proceed as follows: a pore space of a core is saturated with a methanol-enriched liquid phase prior to each test, said phase dissolving any residual amount of n-hexane. A temperature of a filtration system is set according to requirements of the experiment. The methanol-enriched liquid phase goes into the thermodynamic equilibrium with the n-hexane phase. Finally, the n-hexane-enriched phase is injected into the core at a required volumetric flow rate. In this case, however, the researchers don't check the presence of the thermodynamic equilibrium between the phases.

It is known the method for checking thermodynamic equilibrium of gas and condensate, said method comprising steps of using a transparent thermodynamic (PVT) cell and visual observing an interface between gas and liquid phases. This system is described in H. L. Chen, S. D. Wilson, and T. G. Monger-McClure. 1999, Determination of Relative Permeability and Recovery for North Sea Gas-Condensate Reservoirs. SPE Reservoir Eval. & Eng. 2 (4), August 1999.

Many researchers prepare gas and condensate separately prior to the experiment and place containers with phases into a filtration system supposing that both phases are at thermodynamic equilibrium (see, for example, M. Jamiolahmady, M. Sohraby, S. Ireland. 2008, Gas condensate relative permeabilities in propped porous media: coupling versus inertia. SPE Annual Technical Conference and Exhibition, SPE 115726).

SUMMARY

The disclosure provides checking of gas-liquid mixture equilibrium and estimating quality of a gas-liquid (gas-condensate) pair not only prior to but also during and after a filtration experiment. The sequence of steps can be carried out for operative monitoring of the quality of fluids irrespectively of the filtration experiment itself.

In accordance with the method for estimating thermodynamic equilibrium of a gas-liquid mixture, gas and liquid phases with a specified volumetric ratio of phases in a flow and specified flow rates are at least once injected into a multiphase separator. During the injection, gas and liquid phase volumes in the separator are determined and accumulation rates of each phase in the separator are calculated. A discrepancy between phase injection rates and the calculated phase accumulation rates is calculated, based on which the thermodynamic equilibrium is estimated.

BRIEF DESCRIPTION OF DRAWINGS

The invention is illustrated with the drawings, wherein.

DETAILED DESCRIPTION

Figure 1:
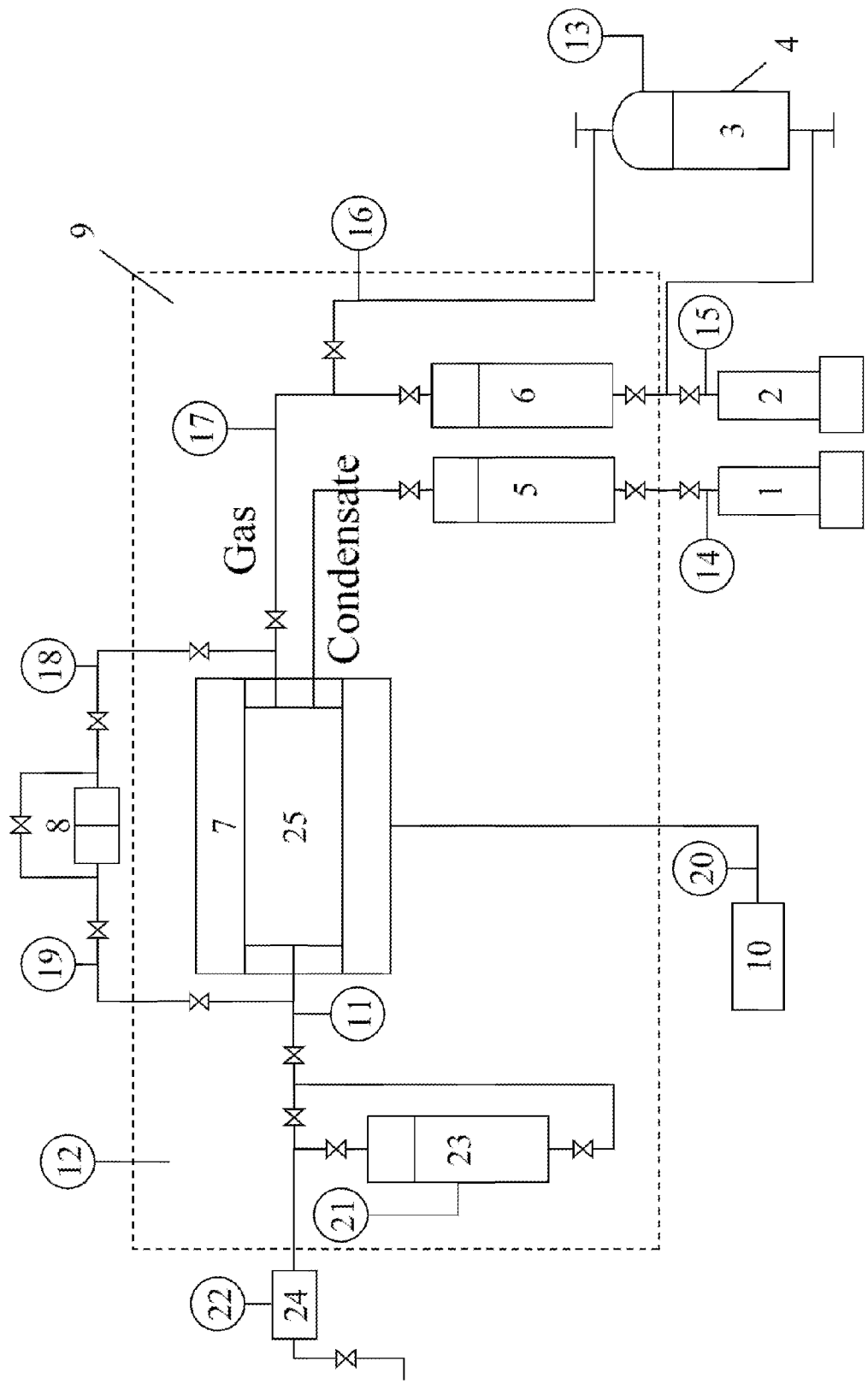
FIG. 1 shows a hydraulic scheme of a core filtration system.

The method can be applied for standard equipment for core filtration (flooding) experiments (for example, Coretest Systems RPS-850, Glo-Bel UIC-5(3)), said equipment comprises: (FIG. 1): 1, 2—piston-type pumps; 3—a high-pressure high-temperature fluid container; 4—a heat tape with heat insulation; 5, 6—piston accumulators; 7—a core holder; 8—a differential pressure gauge; 9—a thermostatically-controlled chamber; 10—an automatic confining pressure support; 11—a temperature sensor; 12, 13—thermocontrollers; 14-22—pressure gauges; 23—a two-phase high-pressure separator with an ultrasonic level indicator; 24—a check valve (a back pressure regulator); 25—a core.

The main unit is the fluid separator 23 designed for a high pressure and a high temperature and provided with the level indicator. The separator can have any construction and operating principles. The separator SFS-032 available from the Coretest Systems was used method testing and implementation. The separator works as follows: mixture of liquids from below arrives at the separator where a denser phase remains in a bottom part of the separator under action of gravity, while a lighter phase is accumulated in a top part, the phases are withdrawn from either the top part or the bottom part, that is, either only the lighter phase or only the denser phase is withdrawn. Then, a position of a phase interface is determined, and a volume of phases in the separator is determined taking into account geometrical dimensions of the separator.

The proposed method for estimating thermodynamic equilibrium of a gas-liquid mixture is based on the following principle: if two or more phases injected to the separator bypassing a core holder are in thermodynamic equilibrium, then a volumetric ratio thereof in the separator should be equal to their volumetric ratio during the injection (specified by parameters of a pump) at the target pressure and temperature.

The method can be implemented as follows.

Before, during or after a filtration (flooding) experiment to estimate a degree of thermodynamic equilibrium between gas and liquid (condensate) phases, there is the following sequence of steps.

The separator 23 is prepared to operation: the separator is filled with both phases at experimental pressure and temperature by simultaneous injection of the gas by the pump 2 and of the condensate by the pump 1 through a bypass line, omitting the core holder 7.

The gas and liquid phases at a given fixed ratio of gas and condensate volumes in the flow and given gas and condensate flow rates are injected by the pumps 2 and 1 using the bypass line and omitting the core holder 7, and simultaneously volumes of the gas and liquid phases went out of the pumps as well as volumes of the phases within the separator are recorded. Industrial equipment in the oil and gas industry widely uses an ultrasonic lever indicator, among others, to measure volumes in the separator. In the latter case, the volumes of the phases within the separator are determined on the basis of a position of the phase interface determined by a time spent by an acoustic wave to achieve said interface, and taking into account geometrical dimensions of the separator as well.

Accumulation rates of the phases in the separator are calculated using total volume data of the injected phases, the position of the phase interface and taking into account a phase to be withdrawn as well, i.e., taking into account also the fact that only a light (gas) phase or only a heavy (condensate) phase is withdrawn from the separator. The total volume of the phases injected by the pumps (the total injection rate) is supposed to be equal to the volume of the phase withdrawn from the separator (the withdrawn phase rate).

To increase the accuracy, the previous steps are repeated at different total injection rates. To improve the reliability of obtained data, it is also possible to inject phases in at different phase flow rates, i.e., at different phase fractions in the flow.

A discrepancy between the phase injection rates and the phase accumulation rates is calculated.

If the discrepancy between the injection rate and the phase accumulation rate is negligible or comparable with an error in determination of a volume by use of the separator, then, the fluid phases are considered as being in the thermodynamic equilibrium and can be used in a core filtration experiment. However if the discrepancy is higher than an acceptable (desirable) limit, then the fluid pair is considered as not being in the thermodynamic equilibrium and should not be used in a core filtration experiment.

Figure 2:
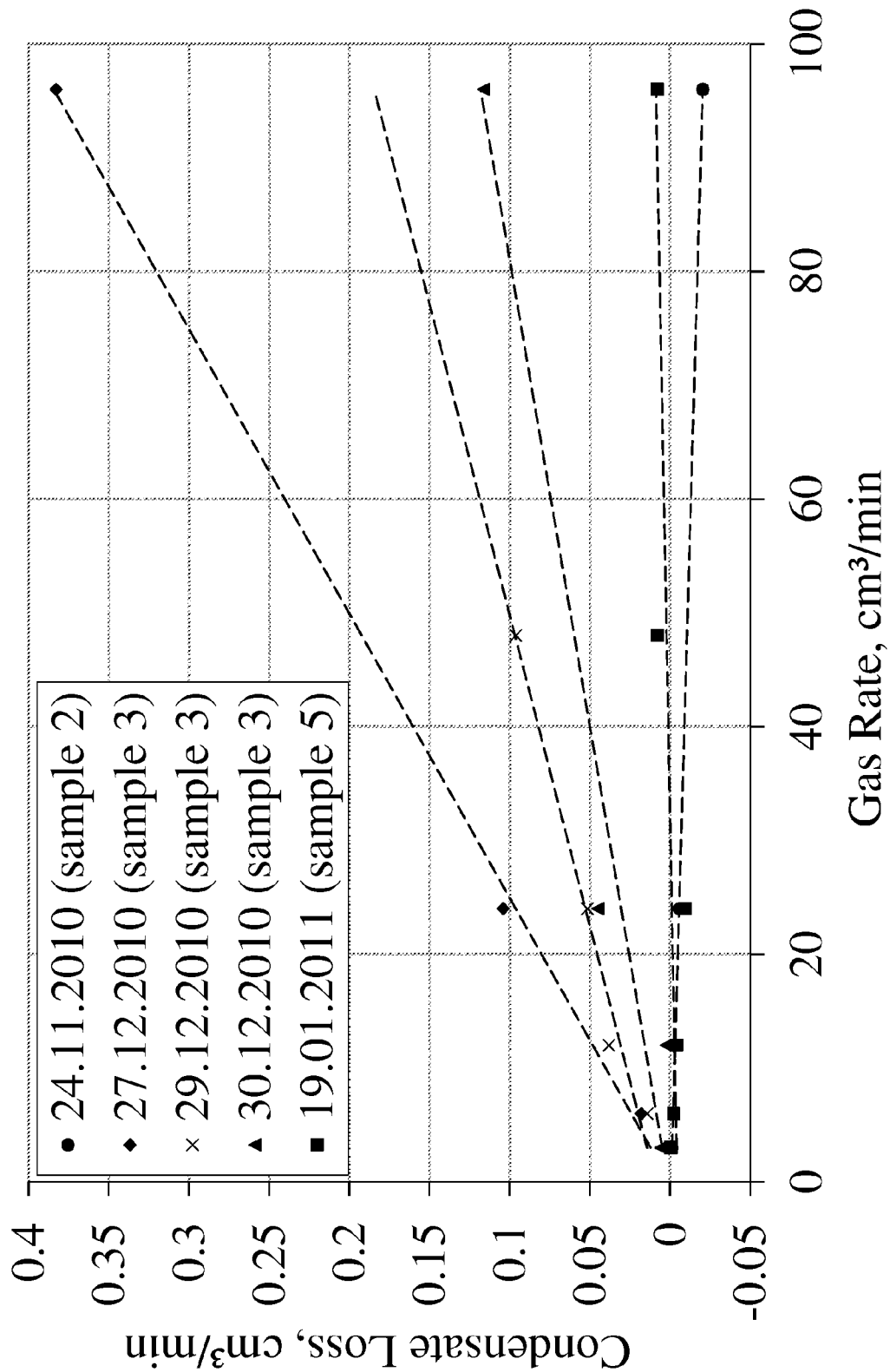
FIG. 2 shows filtration experiment results.

The method was successfully tested and applied during a real gas condensate filtration experiment with results shown in FIG. 2. Before the experiment, all units of the core filtration system shown in FIG. 1 were filled with a gas and a condensate (a sample 2) at experimental pressure and temperature. It is well seen in FIG. 2 that the difference between the injected condensate volume and the condensate volume calculated according to the readings of the separator at the output of the core holder is approximately equal to the error in determination of the volume by the readings of the separator, in other words, is ±0.02 cm$^3$. The sample 2 was consumed during the filtration experiment, and a new sample 3 was prepared in the thermodynamic laboratory and was loaded into the filtration system. As a result of checking the thermodynamic equilibrium degree of phases according to the proposed method, a huge condensate loss (leak) from the separator was detected (the sample 3 in FIG. 2). The sample 3 was considered was considered to be out of thermodynamic equilibrium and unsuitable for using in filtration experiment even after several days of stabilization at the target pressure and temperature (the sample 3 of Dec. 29 and 30, 2010, in FIG. 2). After detailed investigation of preparation procedure of the sample 3 (preparation in the thermodynamic laboratory, transportation, loading into the filtration system), a number of deficiencies and violations were corrected. A final fluid pair (the sample 5 in FIG. 2) was checked for equilibrium using the disclosed method, it was recognized as suitable, and was further used in the filtration experiment.

The invention claimed is:

1. A method for estimating thermodynamic equilibrium of a gas-liquid mixture during a filtration experiment, comprising:
   injecting at least once a gas phase and a liquid phase with a specified volumetric ratio of phases in a flow and specified flow rates into a multiphase separator,
   determining gas and liquid phase volumes in the separator during the injection,
   calculating an accumulation rate of each phase in the separator, and calculating a discrepancy between phase injection rates and the calculated phase accumulation rates, based on which the thermodynamic equilibrium is estimated.

2. The method of claim 1, wherein an ultrasonic acoustic level indicator meter is used to determine gas and liquid phase volumes in the separator.

3. The method of claim 1, wherein subsequent injections are carried out at different injection rates.

4. The method of claim 1, wherein subsequent injections are carried out at different phase fractions in the flow.

* * * * *